(12) United States Patent
Banko

(10) Patent No.: US 6,358,264 B2
(45) Date of Patent: *Mar. 19, 2002

(54) SURGICAL INSTRUMENTS WITH MOVABLE MEMBER

(75) Inventor: William Banko, Mamaroneck, NY (US)

(73) Assignee: Surgical Design Corporation, Long Island City, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/968,830

(22) Filed: Nov. 5, 1997

Related U.S. Application Data

(63) Continuation-in-part of application No. 08/730,851, filed on Oct. 17, 1996, now Pat. No. 5,800,448, which is a continuation-in-part of application No. 08/685,700, filed on Jul. 24, 1996, now abandoned.

(51) Int. Cl.[7] ................................................ A61B 17/32
(52) U.S. Cl. ........................................ 606/169; 606/205
(58) Field of Search ................................ 606/205, 169, 606/174, 170, 83

(56) References Cited

U.S. PATENT DOCUMENTS 5,322,055 A * 6/1994 Davison et al. ................. 601/2
5,819,738 A * 10/1998 Slater .......................... 606/205

* cited by examiner

Primary Examiner—Michael H. Thaler

(57) ABSTRACT

A surgical instrument includes a hollow shaft having an inner passage and a working piece at the distal end of the shaft. A movable member is pivotally mounted on the shaft in cooperative relationship to the working piece and a connecting element extends along the shaft inner passage and has one end exiting thorough an opening in said shaft and connected to the movable member. An actuating member is connected to the connecting element which upon actuation pushes and pulls on the connecting element to move the movable member toward and away from the working piece. An ultrasonic transducer can supply mechanical energy to the shaft to vibrate the working piece, the movable member is mounted to the shaft at a nodal point of the energy pattern along the shaft and the opening in the shaft for exit of the connecting element to the movable member is also at a nodal point.

21 Claims, 5 Drawing Sheets

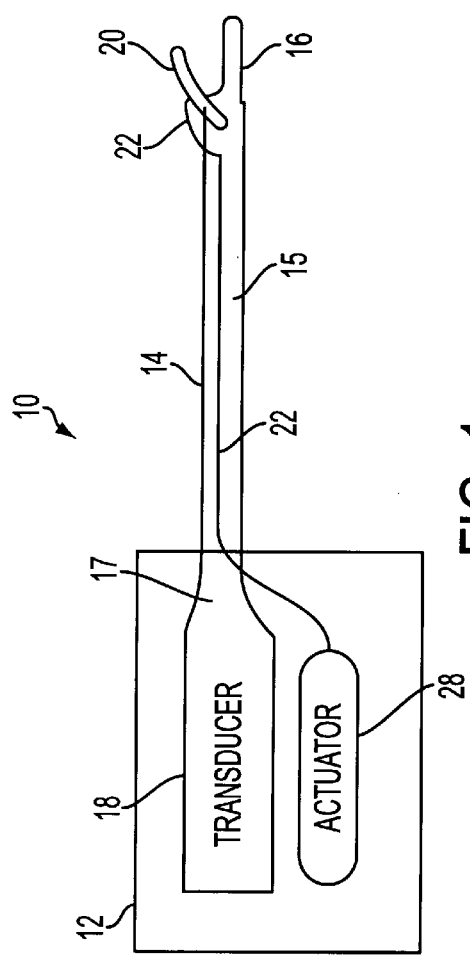
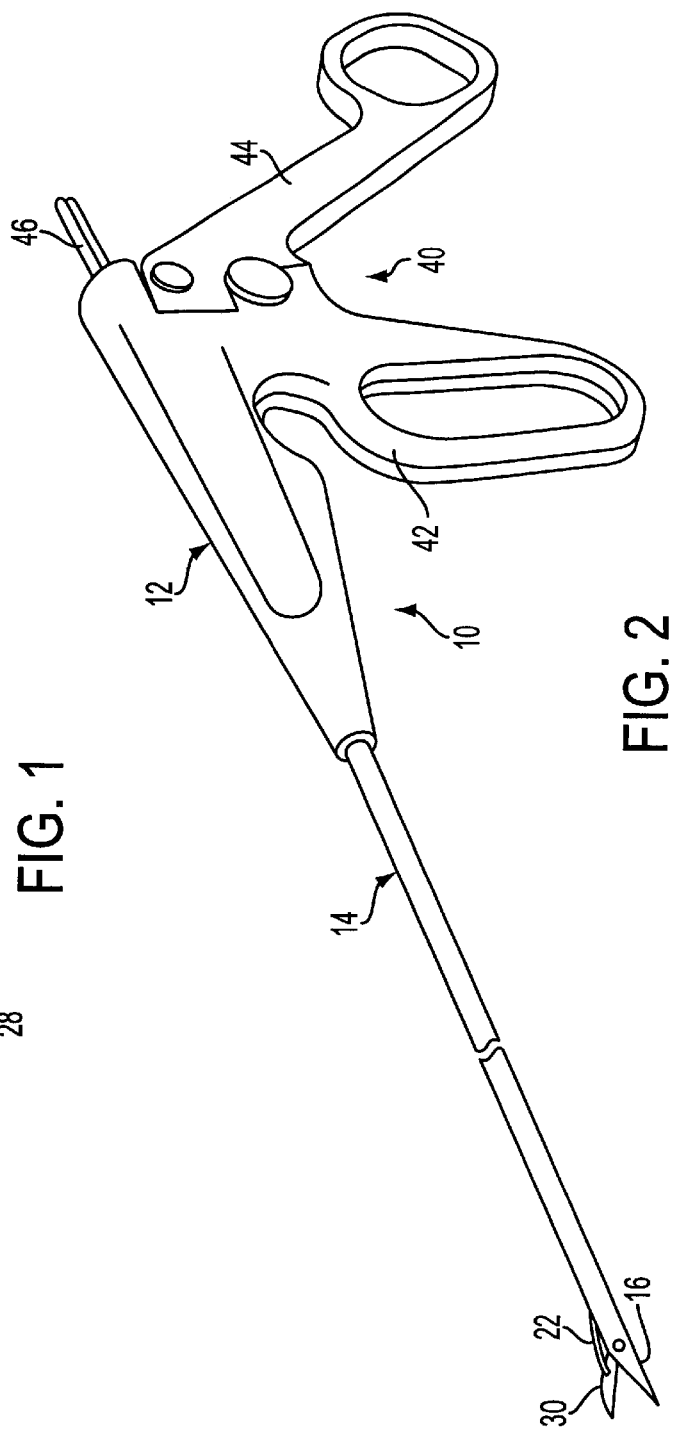
FIG. 1
FIG. 2

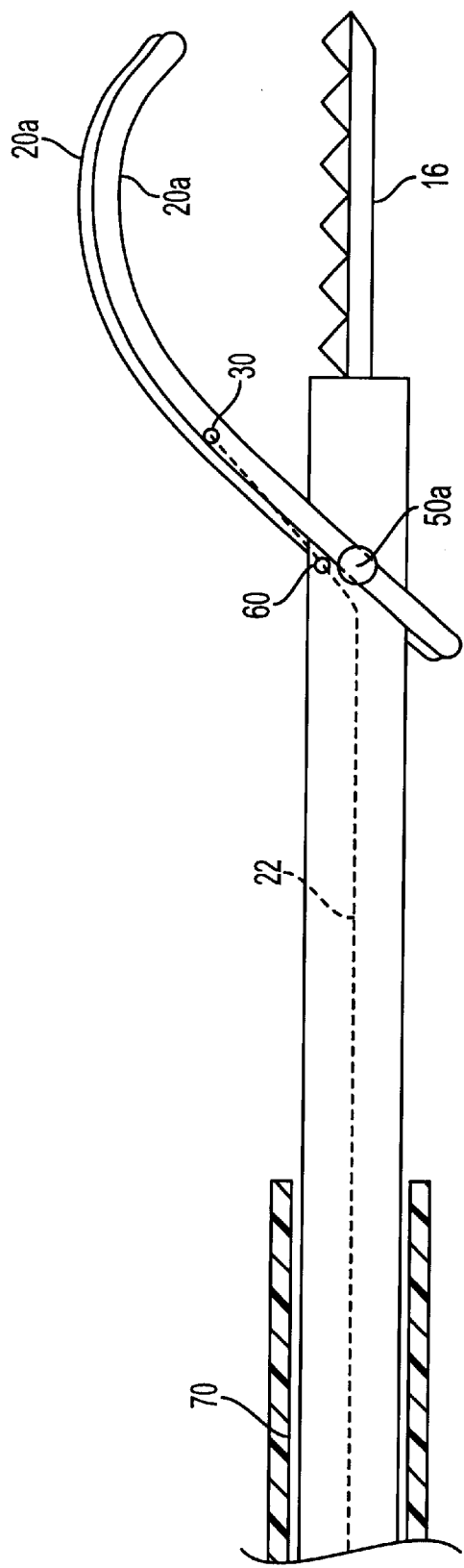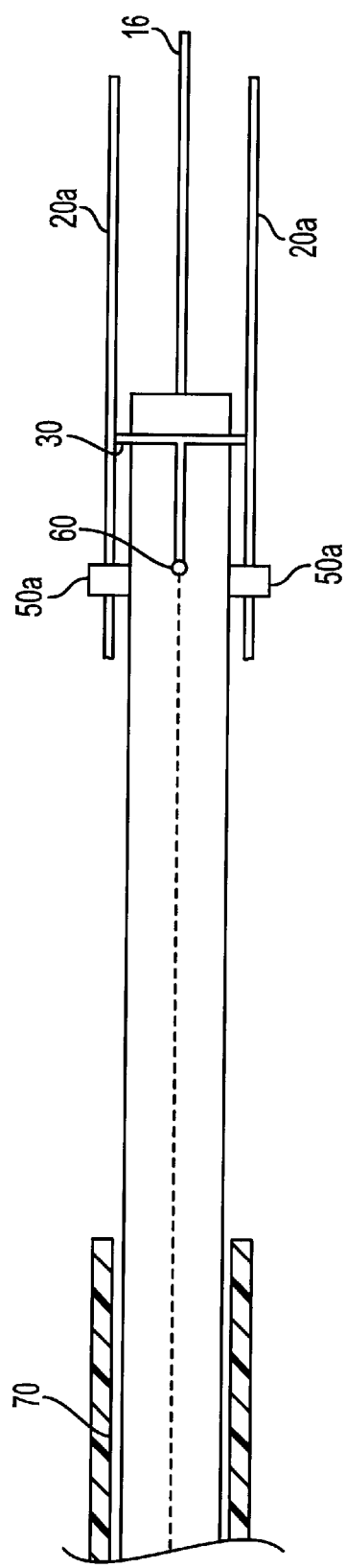

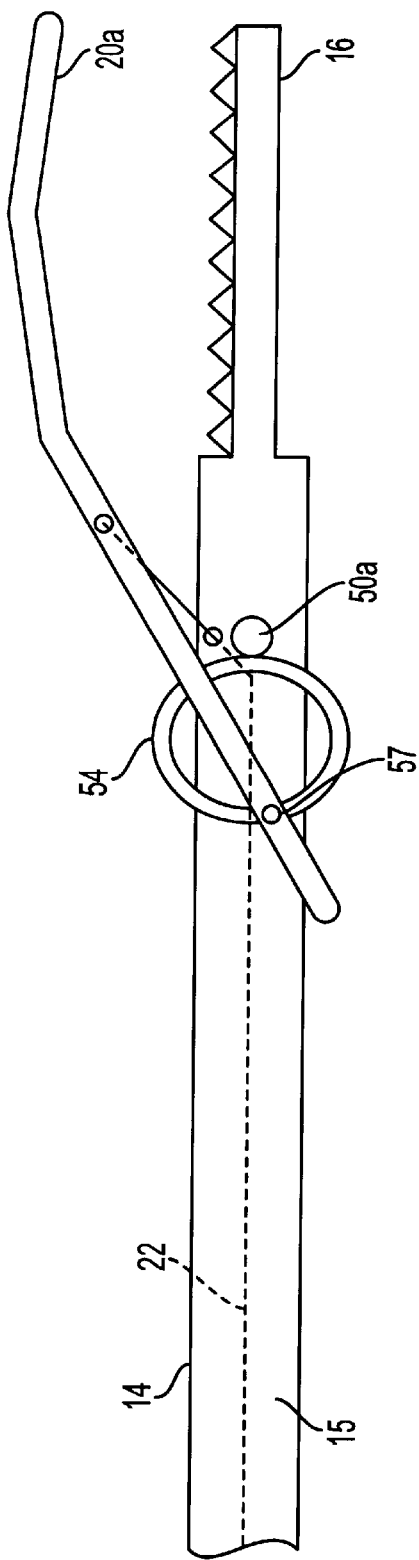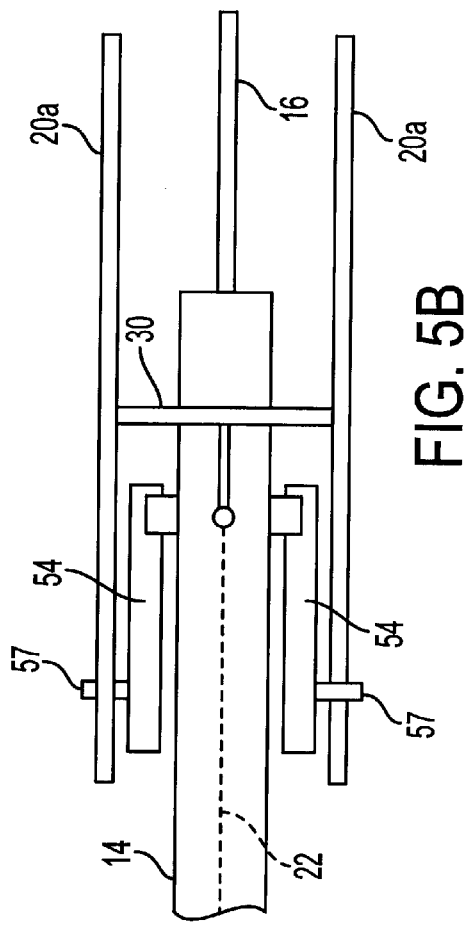

SURGICAL INSTRUMENTS WITH MOVABLE MEMBER

RELATED APPLICATIONS

This application is a continuation-in-part of application Ser. No. 08/730,851, filed Oct. 17, 1996, now U.S. Pat. No. 5,800,448 granted Sep. 1, 1998, which in turn is a continuation-in-part of application Ser. No. 08/685,700, filed Jul. 24, 1996, now abandoned, both of which are assigned to the assignee of the subject application.

BACKGROUND OF THE INVENTION

In the foregoing applications novel surgical scissor instruments are disclosed. The preferred embodiments of the instruments disclosed include a handpiece containing an ultrasonic transducer operative to convert electrical energy into ultrasonic longitudinal vibratory motion. Extending from the handpiece is an elongate portion including a fixed outer tubular member depending from the handpiece. An inner shaft is located in the fixed outer tubular member for reciprocating movement relative to the fixed outer tubular member. A proximal end portion of the inner shaft is operatively connected to the transducer for causing the inner shaft to longitudinally vibrate.

A first cutting member is fixedly mounted to the distal end of the inner shaft and extends from the distal end of the outer tubular member. Longitudinal vibratory motion generated by the transducer affects corresponding longitudinal vibratory motion of the first cutting member, via the inner shaft. A second cutting member is connected to the inner shaft and is pivotable between an open and closed position with respect to the vibrating first cutting member. A second shaft has a first end pivotally connected to the second cutting member for affecting pivotable movement of the second cutting member between the open and closed positions.

SUMMARY OF THE INVENTION

The present invention is directed to improvements in various types of surgical instruments. In accordance with the invention, a hollow shaft is provided which has a working piece, such as a cutting blade, at its distal end. In the case of the instrument being of the ultrasonic type, the proximal end of the hollow shaft receives mechanical energy from an ultrasonic transducer to vibrate the working piece. Such a transducer can be of the piezoelectric or magnetostrictive type. For the latter, a coil of wire receiving electrical energy of a predetermined frequency energizes a stack of laminations. An acoustically tuned connecting body converts the vibrations of the lamination stack into mechanical energy that is conveyed along the length of the shaft to the working piece at the distal end.

In the preferred embodiment, a member is mounted outside of the shaft which is movable relative to the shaft distal end working piece. In the case of the instrument being a scissors, the shaft distal end working piece is one blade and the movable member is the second blade. The movable member is actuated by a connecting element that extends through the inner passage of the hollow shaft and exits through an opening in the shaft to be attached to the movable member. In the case of the instrument being of the ultrasonic type, the movable member preferably is mounted at a nodal point of the mechanical energy that is transmitted along the length of the shaft and the exit opening for the connecting element preferably is also at a nodal point along the shaft. This minimizes the loss of energy to the working piece and also minimizes rubbing friction between the connecting element and the vibrating shaft at the opening.

The instrument has only a single shaft which can be of a very small diameter and no external shafts are needed for the movable member. The principles of the invention are adaptable both to ultrasonic and non-ultrasonic instruments.

OBJECTS OF THE INVENTION

It is therefore an object of the invention to provide improved surgical instruments in which a hollow shaft has a working piece at its distal end and a movable member cooperating with the working piece is actuated by a connecting element extending through the shaft.

Another object is to provide improved ultrasonic surgical instruments in which a hollow shaft vibrated by ultrasonic energy has a working piece at its distal end and a movable member, which is preferably mounted at a nodal point of the vibrating shaft, is actuated by a connecting element extending through an opening in the shaft, also preferably at a nodal point, and has a cooperating action with the shaft working piece.

A further object is to provide a surgical instrument having a hollow shaft housing a plurality of working pieces that can be selected for use by one or more connecting elements extending in the shaft inner passage.

BRIEF DESCRIPTION OF THE DRAWINGS

Other objects and advantages of the present invention will become more apparent upon reference to the following specification and annexed drawings in which:

FIG. 1 is a diagrammatic illustration of a vibratory surgical instrument in accordance with the subject invention;

FIG. 2 is a perspective view of a handle assembly used with the surgical instruments of the invention;

FIGS. 4A and 4B are enlarged side and top views of the operative end of a further embodiment;

FIGS. 5A and 5B are enlarged side and top plan views of the operative end of still a further embodiment of an instrument according to the invention;

DETAILED DESCRIPTION OF THE INVENTION

Figure 3:
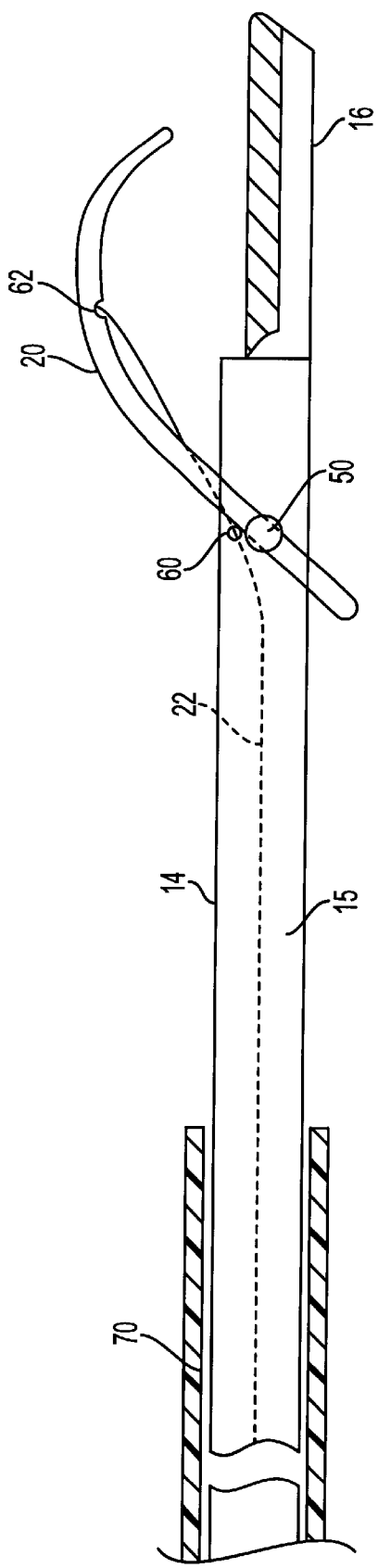
FIG. 3 is an enlarged view of the operative end of an embodiment of an instrument in accordance with the invention.

Referring to FIGS. 1–3, the principles of the invention are illustratively described with reference to an ultrasonic scissors 10. The surgical instruments of the invention are intended to be implemented in a wide variety of surgical instrumentation, e.g., vascular, endoscopic, laparoscopic, etc.

With reference to FIGS. 1–3, the instrument 10 includes a handpiece 12 having a fixed outer tubular (hollow) shaft 14 extending distally therefrom. Shaft 14 has an inner passage 15. While the outer shape of shaft 14 is shown as being cylindrical, it can be of any suitable shape, such as polygonal. It is also of any suitable material, for example, stainless steel. A working member 16, such as one blade of a pair of cooperating scissor blades, is located at the distal end of tubular shaft 14. The working piece 16 can be integrally formed as part of the shaft, such a by machining, or it can be a separate piece that is fastened, such as by welding, to the shaft.

The proximal end of shaft 14 is attached to a handpiece 12 which houses or receives energy from a transducer 18, such as an ultrasonic transducer, to be supplied to the shaft. The transducer 18 comprises any suitable means for converting electrical energy into mechanical longitudinal vibration. For example, the transducer 18 may be of the conventional piezoelectric or magnetostrictive type. The latter has a stack of laminations of a suitable material, such as Nickel. The laminations are connected together at the proximal end of the handpiece 12 and are connected at the stack distal end to one end of an acoustic impedance transformer 17. A wire coil surrounds the lamination stack and supplies electrical energy at a predetermined frequency that is induced in the lamination stack which converts the electrical energy to mechanical energy. The acoustic impedance transformer is a body of metal of suitable shape and thickness necessary to convert the vibrations of the laminations into longitudinal motion. The other end of the acoustic impedance transformer is attached to the proximal end of the hollow shaft 14 for providing longitudinal vibratory motion that is conveyed to the working piece 16. A magnetostrictive type transducer is described in greater detail in commonly assigned U.S. Pat. No. 5,417,203, the disclosure of which is hereby incorporated by reference.

As shown diagrammatically in FIG. 1, a movable member 20 is mounted, in a manner described below, for pivotal motion to cooperate with the working piece 16 at the distal end of shaft 14. In the case of the instrument being a scissors, member 20 is a second scissors blade. The member 20 is moved by a flexible connecting element 22 that extends along the length of the shaft 14 inner passage 15, exits through an opening 60 in the shaft and is connected to member 20 at a point 62. The connecting element 22 is moved in a reciprocating manner by an actuating mechanism 28, described below. The connecting element 22 is of any suitable type and material. For example, it can be a cable or rod of metal or plastic, that is flexible at least at the end exiting from shaft opening 60 and is capable of transmitting force from the actuating mechanism 28 to the movable member 20 upon the connecting element 22 being moved in either direction, that is either pulling on element 22 or pushing it. The diameter of connecting element 22 is selected relative to the diameter of the shaft inner passage 15 and exit opening 60.

Referring to FIG. 2, actuating mechanism 28 is shown as incorporated in a handpiece 12 having a manually operated handle assembly 40 including a fixed handle 42 and a pivoting handle 44. Within a cavity of the handle assembly 40, the proximal end portion of the reciprocating connecting element 22 is operatively connected to pivoting handle 44. Reciprocating motion of pivoting handle 44 by the user of the instrument affects corresponding reciprocating longitudinal motion of connecting element 22 relative to tubular shaft 14 and back and forth motion of movable member 20 relative to the working piece 16.

The transducer 18 can be mounted within the cavity of handpiece 12 with electrical connection to an outside electrical source. In this case, a plug member 46 extending from the handpiece 12 provides electrical energy to the transducer. Alternatively, the transducer 18 can be outside of the handpiece 12. For example, the remote transducer would have a vibrating output shaft which would enter the handpiece 12, such as at point 46, and extend along its length to exit as the shaft 14, as shown.

As is known, the ultrasonic vibratory energy transmitted along the length of the shaft 14 is at a frequency determined by a variety of factors such as, for example, shaft material, dimensions, shape, etc. Located along the length of the shaft are one or more nodal points, that is points at which the amplitude of the vibratory energy is zero, or substantially close thereto. The location of the nodal points correspond to the fundamental frequency and harmonics, principally the second, of the energy propagated along the shaft length. The nodal points can be determined by appropriate design and analysis in accordance with well known principles of ultrasonic technology.

FIG. 3 shows in detail the distal end of one form of the instrument. The working piece 16 at the distal end of the shaft is shown as a straight blade, but it also can be a saw or a clamp. The working piece 16 is vibrated longitudinally by the ultrasonic energy. The movable member 20 is illustratively shown as a scythe shaped blade whose proximal end is pivotally mounted to the shaft 14 on a pivot member 50. The pivot member may be of any suitable type. It is preferred that the pivot 50 be located at a nodal point of the energy along the shaft. Where the member 20 is a single blade, the pivot 50 can be a stud on the outer surface of the shaft and member 20 is slightly offset relative to the working piece 16.

The end portion of connecting element 22 remote from handle 44 extends through an opening 60 in shaft 14. The opening 60 preferably is also at a nodal point of the shaft and can be at the same nodal point as the pivot 50. The distal end of connecting element 22 is connected to the movable member 20 at point 62. By placing each of the pivot mount 50 and the connecting element exit opening 60 at a nodal point along the length of shaft 14, little or no energy is lost by transfer to the pivot mount 50 or connecting element 60. Also, this minimizes rubbing friction between the connecting element 22 and the vibrating shaft 14.

By the user operating the actuating mechanism 28, that is, by reciprocating the pivotal handle 44, the connecting element 22 is moved in a reciprocating manner within the shaft causing the movable member 20 to open and close in an arcuate manner relative to the longitudinally vibrating working piece 16. This causes a cutting action to take place of any object, such as tissue, between elements 16 and 20.

Since shaft 14 is vibrating, as shown in FIG. 3, a protective sleeve 70 is preferably placed around the shaft 14 for a part of its length up to the distal end to protect the user from any heat built up on the shaft. Sleeve 70 can be of any suitable material, for example, TEFLON, KYNAR, etc.

FIGS. 4A and 4B show another embodiment of the invention wherein the same reference numbers are use for the same components previously described. Here, the working piece 16 at the distal end of the shaft 14 is shown as a saw type blade, although any suitable cutting instrument, or clamp, can be used. A pair of pivot mounting studs 50a are fastened, such as by welding, to the outer surface of the shaft 14, preferably at a nodal point. The studs 50a preferably lie along a diametrical line through the shaft. The movable member is formed by a pair of spaced curved arms 20a, which can be blades or clamp members. Each of the arms 20a has its proximal end pivotally mounted to a respective one of the studs 50a. A cross-piece 30 connects the two movable arms 20a. The end of connecting element 22 which protrudes from the shaft opening 60, which also preferably is at a nodal point, is connected to the cross-piece 30. The cross-piece 30 either can overlie the shaft, as shown, or it can overlie the working piece 16.

The operation of the instrument of FIGS. 4A–4B is as previously described. That is, when the user actuates the instrument pivotal handle 44, the connecting element 22 is longitudinally reciprocated within the shaft passage to move the cross-piece 30 and thereby move the two arms 20a about the pivots 50a back and forth relative to the working piece 16. If the arms 20a are clamp members, they hold the object being operated on against the vibrating working piece 16 to cut the object.

FIGS. 5A and 5B show a further embodiment of the invention which is similar to that of FIGS. 4A and 4B in the use of the twin movable arms 20a connected by the cross-piece 30. Here, an extender 54 is connected to each of the pivot mounting studs 50a and extends proximally of the shaft. As explained above, the studs 50a preferably are mounted at a node of the energy with respect to the shaft. Thus, no energy is transmitted to an extender 54. Each extender 54 is shown as being generally circular in shape, although any other shape can be utilized. As shown, each of the arms 20a is pivotally mounted to an extender 54 at pivot point 57. The extenders 54 permit the configuration of the movable member 20a to be more varied in shape and also can provide greater leverage for the reciprocating operation of the arms 20a by the connecting element 22.

The operation of the instrument of FIGS. 5A–5B is the same as that described with respect to FIG. 4.

Figure 6A:
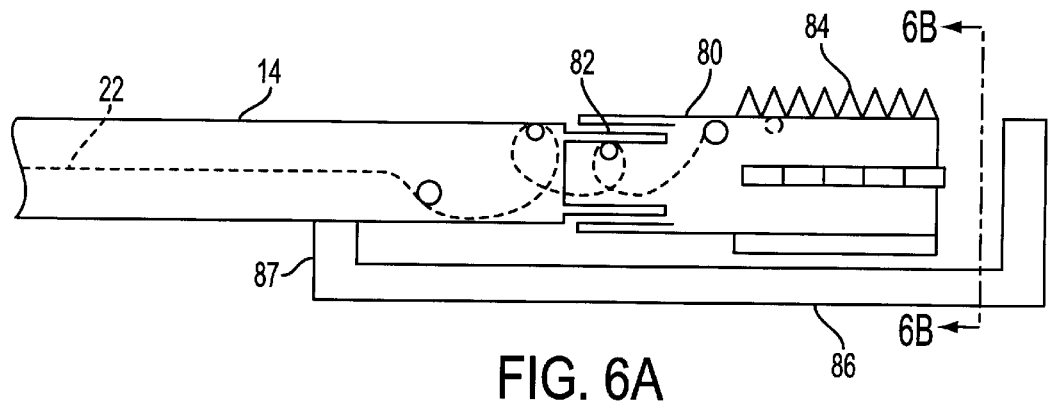
FIGS. 6A and 6B are an enlarged side view and an end view along line A—A of an embodiment of the invention in which working pieces are selected using a rotatable mount.
Figure 6B:
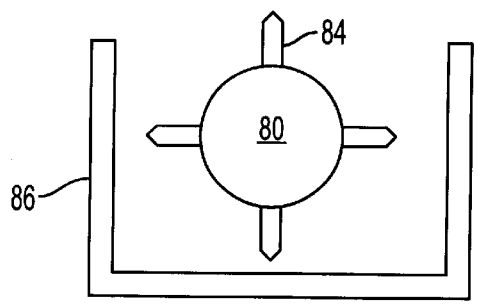

FIGS. 6A and 6B show a further embodiment of the invention in which a head 80 is rotatably mounted at the distal end of shaft 14. The head has a plurality of different types of cutting implements 84 spaced around its outer surface. Four such implements are shown spaced apart by 90°, although any suitable number of implements of any suitable type and shape, can be spaced around at any suitable angular orientation. A protective cover 86 has an end 87 connected to shaft 14, also preferably at a nodal point. The cover extends over the head 22 and permits exposure to an operative position of only one of the implements 84.

The mount 82 for the head 80 to the end of the shaft 14 is preferably of the rotatable detent type. The mount 82 has a mechanism which is actuated by the connecting element 22 when the user actuates the pivotal handle member 44. The mechanism converts the linear pulling or pushing motion of the connecting element 22 produced by actuating handle 44 into rotational motion of the head 80. Thus, for example, each pull (or push) of the handle 44 will rotate head 80 by one detent stop to expose a different implement 84 through the protector 86. If the instrument is of the ultrasonic type, the head 80 and the working implements will be vibrated longitudinally and the exposed implement 84 will be available to achieve a cutting action.

If desired, in the embodiment of FIG. 6, a second connecting element can be passed through the shaft and a movable member 20, such as shown in FIGS. 1–5, can be attached to the shaft to be actuated by the second connecting element.

Figure 7B:
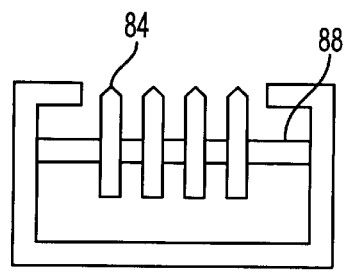
FIGS. 7A and 7B are an enlarged side view and an end view along line A—A of the operative end of an embodiment in which a working piece is selected by actuation of a connecting element.
Figure 7A:
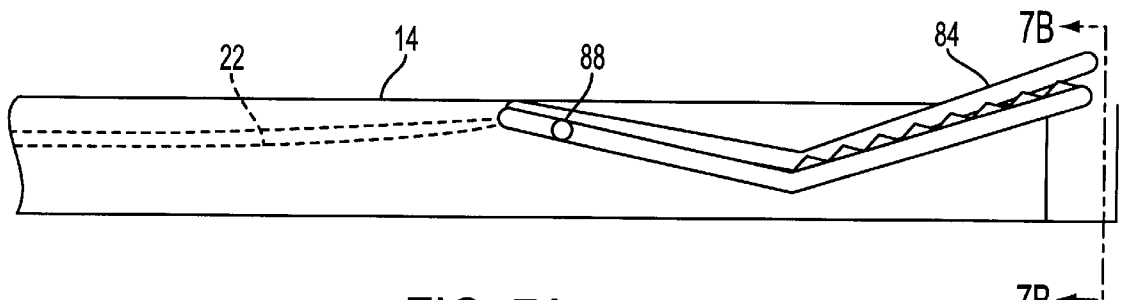

FIGS. 7A and 7B show another embodiment of the invention in which there are a plurality of implements 84, two such implements being illustrated, pivotally mounted at the end of the shaft 14, which can be vibrating or stationary, on an axle 88. A respective connecting element 22 is connected to each implement 84. The handle 40 of FIG. 2 would have two triggers, one for each connecting element, or a trigger mechanism that can be selectively connected to a connecting element. Actuating a connecting element, by pulling it back away from the shaft distal end, causes the respectively connected implement 84 to rotate on axle 88 and extend outwardly of the shaft and be available for cutting action. Pushing on the connecting element retracts the respective implement 84 back into the shaft. Here also, the shaft 14 can be vibrated by energy from a transducer so that the exposed implement will have a cutting action. Here also, a movable member can be attached to the shaft 14 as previously described.

It should be appreciated that the surgical instruments of the invention are compact, lightweight and easy to use. The instruments can be used with one hand, thus freeing the other hand for performance of other surgical tasks.

I claim:

1. A surgical instrument comprising:
   a hollow shaft having an inner passage;
   a working piece mounted to the distal end of said shaft;
   an ultrasonic transducer to produce vibratory mechanical energy that is applied to said shaft to be deliberately propagated along said shaft to vibrate said working piece, wherein the vibratory mechanical energy along said shaft has a pattern with at least one nodal point of reduced energy;
   a movable member pivotally mounted on said shaft at a said nodal point of the vibratory mechanical energy in cooperative relationship to said working piece;
   a connecting element extending along the shaft inner passage having one end exiting thorough an opening in said shaft and connected to said movable member; and
   an actuating member connected to said connecting element which upon actuation pushes and pulls on said connecting element to move said movable member toward and away from said working piece.

2. An ultrasonic instrument as in claim 1 wherein said opening for the exit of said connecting element one end from said shaft inner passage is at a said nodal point.

3. An ultrasonic surgical instrument as in claim 2 wherein said movable member pivotal mounting and said opening for the exit of said connecting element one end from said shaft inner passage are at the same nodal point.

4. An ultrasonic surgical instrument as in claim 1 wherein each of said working piece and said movable member comprises a cutting implement, said working piece being vibrated relative to said movable member.

5. An ultrasonic surgical instrument as in claim 1 wherein said movable member comprises a pair of spaced arms.

6. An ultrasonic surgical instrument as in claim 5 wherein said pair of arms form a clamp to hold an object between said clamp and said vibrating working piece.

7. An ultrasonic surgical instrument as in claim 5 wherein said vibrating working piece has a cutting edge and said pair of arms have cutting edges in opposition to said working piece cutting edge.

8. An ultrasonic surgical instrument as in claim 5 further comprising a cross-piece connecting said pair of arms.

9. An ultrasonic surgical instrument as in claim 8 wherein said one end of said connecting element is connected to said cross-piece to move said movable member.

10. An ultrasonic instrument as in claim 1 further comprising an extension piece connected to said shaft at a said nodal point and extending toward the proximal end of said shaft, said movable member being pivotally mounted to said extension piece.

11. A surgical instrument as in claim 10 further comprising:

a second connecting element extending along the shaft inner passage having one end exiting thorough an opening in said shaft and connected to said movable member; and an actuating member connected to said second connecting element which upon actuation pushes and pulls on said second connecting element to move said movable member toward and away from said working piece.

12. A surgical instrument comprising:

a hollow shaft having an inner passage;

a working piece at the distal end of said shaft;

an ultrasonic transducer to produce vibratory mechanical energy along said shaft to vibrate said working piece;

a movable member pivotally mounted on said shaft in cooperative relationship to said working piece;

a connecting element extending along the shaft inner passage having one end exiting thorough an opening in said shaft and connected to said movable member; and p1 an actuating member connected to said connecting element which upon actuation pushes and pulls on said connecting element to move said movable member toward and away from said working piece, wherein said working piece at the distal end of said shaft comprises:

a head having a plurality of working implements mounted therearound;

a rotatable mount connecting said head to an end of said shaft;

a mount actuating element extending along the shaft inner passage having one end connected to actuate said rotatable mount; and an actuating member connected to said mount actuating element which upon actuation pushes and pulls on said mount actuating element to actuate said mount to rotate said head to rotate said working implements relative to said shaft.

13. A surgical instrument as in claim 12 wherein said ultrasonic transducer produces mechanical energy along said shaft to vibrate said head and the working implements thereon.

14. A surgical instrument as in claim 13 wherein the vibratory mechanical energy along said shaft has a pattern with at least one nodal point of reduced energy, said movable member being pivotally mounted to said shaft at a said nodal point.

15. A surgical instrument as in claim 12 wherein the vibratory mechanical energy along said shaft has a pattern with at least one nodal point of reduced energy, and wherein said opening for the exit of said connecting element one end from said shaft inner passage is at a said nodal point.

16. A surgical instrument as in claim 12 further comprising a protective cover over said head to expose a selected one of said working implements into an operative position upon rotation by said head.

17. A surgical instrument comprising:

a hollow shaft having an inner passage;

a working piece at the distal end of said shaft;

an ultrasonic transducer to produce vibratory mechanical energy along said shaft to vibrate said working piece;

a movable member pivotally mounted on said shaft in cooperative relationship to said working piece;

a connecting element extending along the shaft inner passage having one end exiting thorough an opening in said shaft and connected to said movable member; and an actuating member connected to said connecting element which upon actuation pushes and pulls on said connecting element to move said movable member toward and away from said working piece, wherein said working implement comprises:

a plurality of working implements pivotally mounted in said passage at the distal end of said shaft, said shaft distal end having an opening through which a said working implement can project; and a plurality of connecting elements extending along the shaft inner passage, each said connecting element connected to a selected one of said working implements, actuation of a connecting element moving the connected working implement to project through said shaft opening to a position external of said shaft.

18. A surgical instrument as in claim 17 wherein said ultrasonic transducer produces mechanical energy along said shaft to vibrate said working implements.

19. A surgical instrument as in claim 18 wherein said ultrasonic transducer produces mechanical energy along said shaft that has a pattern with at least one nodal point of reduced energy and said movable member is mounted to said shaft at a said nodal point.

20. A surgical instrument as in claim 18 wherein said ultrasonic transducer produce mechanical energy along said shaft that has a pattern with at least one nodal point of reduced energy and wherein said opening for the exit of said connecting element one end from said shaft inner passage is at a said nodal point.

21. A surgical instrument as in claim 17 further comprising:

a second connecting element extending along the shaft inner passage having one end exiting thorough an opening in said shaft and connected to said movable member; and an actuating member connected to said second connecting element which upon actuation pushes and pulls on said second connecting element to move said movable member toward and away from said working piece.

* * * * *